United States Patent [19]
Kanda et al.

[11] Patent Number: 5,054,916
[45] Date of Patent: * Oct. 8, 1991

[54] LIVER FUNCTION TESTING APPARATUS

[75] Inventors: Masahiko Kanda; Kunio Awazu, both of Osaka, Japan

[73] Assignee: Sumitomo Electric Industries, Ltd., Osaka, Japan

[*] Notice: The portion of the term of this patent subsequent to Oct. 8, 2008 has been disclaimed.

[21] Appl. No.: 268,735

[22] Filed: Nov. 8, 1988

[30] Foreign Application Priority Data

Nov. 13, 1987 [JP] Japan .................. 62-287678

[51] Int. Cl.$^5$ .......................... G02N 33/48
[52] U.S. Cl. ....................... 356/39; 356/41; 128/633; 128/666
[58] Field of Search .................. 356/39–42, 356/51, 72, 410, 418, 320, 39; 250/218, 528; 128/665–667, 633

[56] References Cited

U.S. PATENT DOCUMENTS

| | | |
|---|---|---|
| 3,677,648 | 7/1972 | Dorsch . |
| 4,017,192 | 4/1977 | Rosenthal . |
| 4,100,416 | 7/1978 | Hirschfeld ............ 356/307 |
| 4,266,554 | 5/1981 | Hamaguri ............ 356/41 |
| 4,569,589 | 2/1986 | Neufeld . |
| 4,602,641 | 7/1986 | Feinberg . |
| 4,905,703 | 3/1990 | Kanda et al. ......... 128/666 |

FOREIGN PATENT DOCUMENTS 0276477 8/1988 European Pat. Off. .
58649 12/1985 Japan .

OTHER PUBLICATIONS

Article entitled: "Indocyanine Green Liver Function Studies on Women Taking Progestins", by N. K. Takaki et al., Obstetrics and Gnecology, 0326, pp. 220–227.

Primary Examiner—Richard A. Rosenberger
Assistant Examiner—Hoa Pham
Attorney, Agent, or Firm—W. G. Fasse; D. H. Kane, Jr.

[57] ABSTRACT

In a liver function testing apparatus, light sources (11, 12) expose vital tissue (15) to first light of a wavelength capable of being absorbed by a specific dye dosed into blood of the vital tissue to be taken in and removed by the liver, and second light of a wavelength not capable of being absorbed by the specific dye. Optical pulses obtained from the vital tissue are received by a light receiving element (13), the output of which is sampled by an A/D converter (30) for converting the analog output signals into digital signals. A biocalibration is preformed on the basis of variable components in the blood. For this purpose a CPU (34) determines coefficients for first and second regression line expressions before and after an injection of the specific dye. The coefficients are provided by first and second photoelectric conversion signals. A value correlated with a specific dye concentration in the blood is processed on the basis of sampling signals during a prescribed period after injecton of the specific dye to provide the coefficients for the regression line expressions. The obtained coefficients are processed by using the method of least squares for obtaining a blood plasma disappearance rate of the specific dye and a retention rate for a prescribed length of time following an injection.

14 Claims, 12 Drawing Sheets

FIG. 1

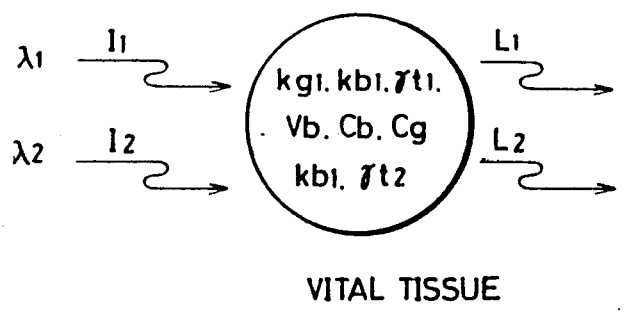

VITAL TISSUE

- $kg_1$ : ABSORPTION COEFFICIENT OF SPECIFIC DYE (WAVELENGTH : $\lambda_1$)
- $kb_1$ : ABSORPTION COEFFICIENT OF BLOOD AT WAVELENGTH $\lambda_1$
- $kb_2$ : ABSORPTION COEFFICIENT OF BLOOD AT WAVELENGTH $\lambda_2$
- $\gamma t_1$ : ABSORBANCE OF TISSUE AT WAVELENGTH $\lambda_1$
- $\gamma t_2$ : ABSORBANCE OF TISSUE AT WAVELENGTH $\lambda_2$
- $V_b$ : BLOOD VOLUME IN SAMPLE
- $C_b$ : BLOOD CONCENTRATION IN SAMPLE
- $C_g$ : SPECIFIC DYE CONCENTRATION IN SAMPLE $Y = .869716 \ X$
$+ .861895$ $r = .999438$

FIG. 9

X X X X X X X X X X X
X ICG MONITOR CALIBRATION X
X X X X X X X X X X X

Please attach the Sensor

FIG. 10

Please prepare the ICG INJECTION

OK → START

FIG. 11

1 → 2 → 3 → 4 → 5 sec

LIVER FUNCTION TESTING APPARATUS

FIELD OF THE INVENTION

The present invention relates to a liver function testing apparatus, and more specifically, it relates to a liver function testing apparatus for automatically performing measurements for testing/diagnosing a liver function by injecting a specific color dye into the patient's bloodstream, which is selectively taken in and removed only by the liver. A blood plasma disappearance rate and a retention rate are determined.

BACKGROUND INFORMATION

In general, the blood plasma disappearance rate and the retention rate have been measured by a method of blood collection through use of indocyanine green (hereinafter referred to as ICG) serving as specific dye. According to this method, an intravenous injection of ICG is given to a testee and blood collections are made three times after lapses of five, ten and fifteen minutes after the injection, and blood serum is separated upon coagulation of a blood clot so that an absorbance at a wavelength of 805 nm is measured through a spectrophotometer to obtain ICG concentration values in the blood serum after the lapses of five, ten and fifteen minutes from a previously obtained calibration curve representing an ICG concentration in blood as a function of absorbance. Thus, it is possible to calculate the blood plasma disappearance rate and the retention rate. In recent years, a method of changing the quantity of the ICG injection to measure the blood plasma disappearance rate several times has been widely used for obtaining an index expressing an amount of hepatic cell function $R_{MAX}$ (removal maximal).

Japanese Patent Publication Gazette No. 58649/1985 has already proposed a method of measuring the blood plasma disappearance rate and the retention rate without performing any blood collection. According to said method, light is applied through the body surface of an organism, which in turn transmits light of a wavelength having a high ICG absorption sensitivity and light of a wavelength having substantially no ICG absorption sensitivity. The respective quantities of transmitted light are measured to obtain the blood plasma disappearance rate and the retention rate as a function of elapsed time (dye disappearance curve) of the light quantities.

In the aforementioned first mentioned method requiring the collection of blood samples, it is necessary to correctly measure the blood collection time after injection. However, the time cannot be accurately measured in fact, and the practical measuring of the index expressing the amount of hepatic cell function $R_{MAX}$ has been complicated in its adaptation to the theory. Further, the testee has been subjected to heavy mental and physical burdens by the repeated taking of blood samples. In addition, the index $R_{MAX}$ method of measuring the blood plasma disappearance rate several times by changing the quantity of ICG injection requires the taking of more than ten blood samples, whereby the burdens on the testee are further increased.

According to the second mentioned measuring method which does not require the taking of any blood samples disclosed in Japanese Patent Publication Gazette No. 58649/1985, the output of a sensor actually attached to an organism, fluctuates under the influence of such facts as blood flow disturbances caused by a compression on a blood vessel, vibrations of the organism that is tested, pulsations in the organism, changes in the blood volume in the vital tissue. The blood volume in each part of a vital tissue changes due to movements, for example, by merely vertically moving an arm, etc., whereby a correct dye disappearance curve cannot be obtained. Consequently, the blood plasma disappearance rate and the retention rate obtained by the curve cannot be recognized as being correct.

SUMMARY OF THE INVENTION

Accordingly, a main object of the present invention is to provide a liver function testing apparatus which can avoid the adverse effects of the above mentioned fluctuating influences, such as blood flow disturbances, vibrations of an organism, pulsations in the organism, and changes of the blood volume in the organism, to enable a correct measurement.

Briefly stated, vital tissue is exposed to first light of a wavelength absorbed by a specific dye dosed into the blood of the vital tissue of the person to be tested and removed by the liver, and a second light of a wavelength not absorbed by the specific dye and first and second photoelectric conversion signals corresponding to the first light and the second light obtained from the vital tissue, are sampled a plurality of times so that first and second coefficients of first and second regression line expressions between the first and second photoelectric conversion signals are determined on the basis of variable components in the blood included in the first and second photoelectric conversion signals sampled a plurality of times before and after an injection of the specific dye to perform biocalibrations. Further, a value correlated with a specific dye concentration in the blood is processed on the basis of the sampling signals applied a plurality of times in a prescribed period after an injection of the specific dye, and the determined coefficients of the first and second regression line expressions are used to obtain a coefficient of a simulation function as a function of time by applying to said dye concentration value, the method of least squares, thereby to obtain a blood plasma disappearance rate of the specific dye and a retention rate of the specific dye in a prescribed or determined period of time.

Thus, according to the present invention, the correct time management of the disappearance curves of the specific dye makes it possible to obtain correct data. Further, the blood plasma disappearance rate and the retention rate can be obtained without the need for taking several blood samples as is the case in the conventional blood correction method. Rather, the invention uses a large number of data obtained from the disappearance curves, thereby improving the reliability of the data.

In a preferred embodiment of the present invention, the second coefficient is obtained within a prescribed period of time following an injection of the specific dye and allowing for an arbitrary short period after time to permit the specific dye to be uniformly distributed in the blood.

Further, first dimensionless constants $A_1$ and $B_1$ are obtained by performing a regression line analysis in accordance with the following operation expression:

$$\log CL_1 = A_1 \cdot \log CL_2 + B_1$$

wherein $CL_1$ and $CL_2$ represent average voltage values of first and second photoelectric conversion signals caused by the applied first and second light quantities $L_1$ and $L_2$ and sampled a plurality of times before injection of the specific dye.

Second dimensionless constants $A_2$ and $B_2$ are obtained by performing a regression line analysis in accordance with the following operation expression:

$$\log CL_{1'} = A_2 \cdot \log CL_{2'} + B_2,$$

wherein $CL_{1'}$ and $CL_{2'}$, represent average voltage values of the first and second photoelectric conversion signals caused by the applied first and second light quantities $L_1$ and $L_2$ and sampled a plurality of times after a lapse of a prescribed period of time following the injection of the specific dye, whereby $$\log L_{10} = (A_1 \cdot B_2 - A_2 \cdot B_1)/(A_1 - A_2)$$

is obtained as a blood free point. $A_1$, $A_2$, $B_1$, and $B_2$ are the above mentioned dimensionless constants determined, as to $A_1$ and $B_1$, prior to the dye injection and, as to $A_2$ and $B_2$, after the dye injection.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 1 to 4 are diagrams for illustrating the principle of biocalibration employed in the present invention;

FIGS. 8A to 8D are flow charts for concretely illustrating the operation of the embodiment, in which FIG. 8A shows a data sampling subroutine, FIG. 8B shows a biocalibration mode, FIG. 8C shows an initialization mode and FIG. 8D shows a measurement mode;

FIGS. 9 to 12 are illustrative of exemplary displays on a display part or screen as shown in FIG. 5;

DESCRIPTION OF THE PREFERRED EMBODIMENTS

Before explaining embodiments of the present invention, the principle of biocalibration employed in the present invention will first be explained.

FIGS. 1 to 4 are diagrams for illustrating the principle of the biocalibration in the present invention.

It is assumed that symbols $I_1$ and $I_2$ indicate quantities of light having a wavelength $\lambda_1$ which is largely absorbed by the specific dye, and light of a wavelength $\lambda_2$ which is not absorbed by the specific dye incident upon vital tissue. The symbols $L_1$ and $L_2$ indicate the above mentioned light quantities after passage through a prescribed optical path in the vital tissue. Relationships between the incident light quantities $I_1$ and $I_2$ and the passing light quantities $L_1$ and $L_2$ with reference to the injected specific dye, are as follows:

$$\log I_1/L_1 = kg_1 \cdot Cg \cdot Vb + f_1(Cb, Vb) + \gamma t_1 \quad (1)$$

$$\log I_2/L_2 = f_2(Cb, Vb) + \gamma t_2 \quad (2)$$

Respective coefficients and variables are shown in FIG. 1. Symbols $f_1$ and $f_2$ represent functions which are determined by blood characteristics at the wavelengths $\lambda_1$ and $\lambda_2$.

On the other hand, relationships between the incident light quantities $I_1$ and $I_2$ and the passing light quantities $L_1$ and $L_2$ before the injection of the specific dye are as follows:

$$\log I_1/L_1 = f_1(Cb, Vb) + \gamma t_1 \quad (3)$$

$$\log I_2/L_2 = f_2(Cb, Vb) + \gamma t_2 \quad (4)$$

Figure 2:
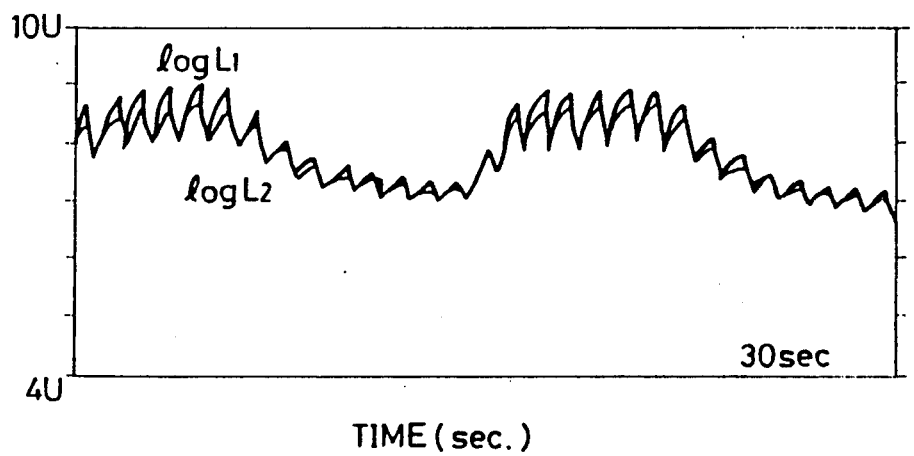
Figure 3:
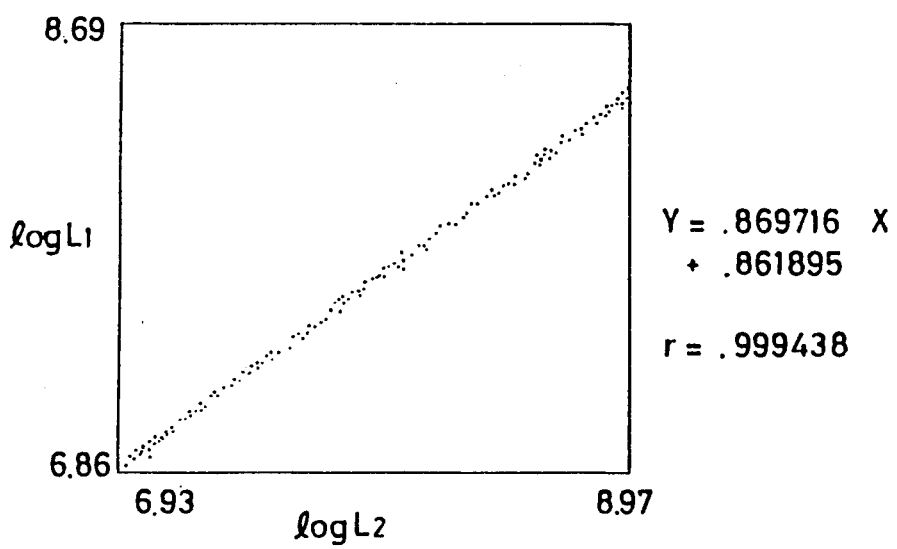

The relationships between the passing light quantities $L_1$ and $L_2$ prior to an actual injection of the specific dye is measured and shown in FIGS. 2, whereby a logarithmic plotting provides a linear relationship as shown in FIG. 3. The shown data represent the case of attaching a sensor to an organism and fluctuating the blood volume in the organism. It has been confirmed that such linearity has a reproducibility with no individual differences.

Then, the expressions (3) and (4) would appear as follows, as expressed by a straight line ① shown in FIG. 4:

$$\log L_1 = A_1 \log L_2 + B_1 \quad (5)$$

That is, the same can be expressed as follows, by using the expressions (3) and (4):

$$\log I_1 - \{f_1(Cb, Vb) + \gamma t_1\} = A[\log I_2 - \{f_2(Cb, Vb) + \gamma t_2\}] + B \quad (6)$$

where $Cb$ represents a blood concentration in a sample and $Vb$ represents a blood volume in the sample.

A function C obtained by multiplying the concentration of the specific dye by the blood volume in the sample and the absorption coefficient of the specific dye, by using the expressions (1) and (2) after injection of the specific dye can be expressed as follows:

$$C = \log L_1 = [A \cdot \log L_2 + B] \quad (7)$$

The function C as defined by the expression (7) is then written as follows:

$$C = \log I_1 - kg \cdot Cg \cdot Vb \, [f_1(Cb, Vb) + \gamma t_1] - A[\log I_2 - \{f_2(Cb, Vb) + \gamma t_2\}] - B \quad (8)$$

Through the expression (6) we have:

$$C = -kg \cdot Cg \cdot Vb \quad (9)$$

Hence, it is understood that a signal of the function C can be obtained by using FIG. 3 as a calibration curve.

As to the function C, however, although the coefficient kg is constant, it can be considered that the blood volume Vb in each part is changed from time to time, and hence, if the blood volume Vb in a sample generated by the sensor attached to the vital tissue, is changed, the amount of the specific dye is also changed in proportion to the change in the blood volume, so that the dye concentration remains unchanged. This is typically shown in FIG. 4.

Figure 4:
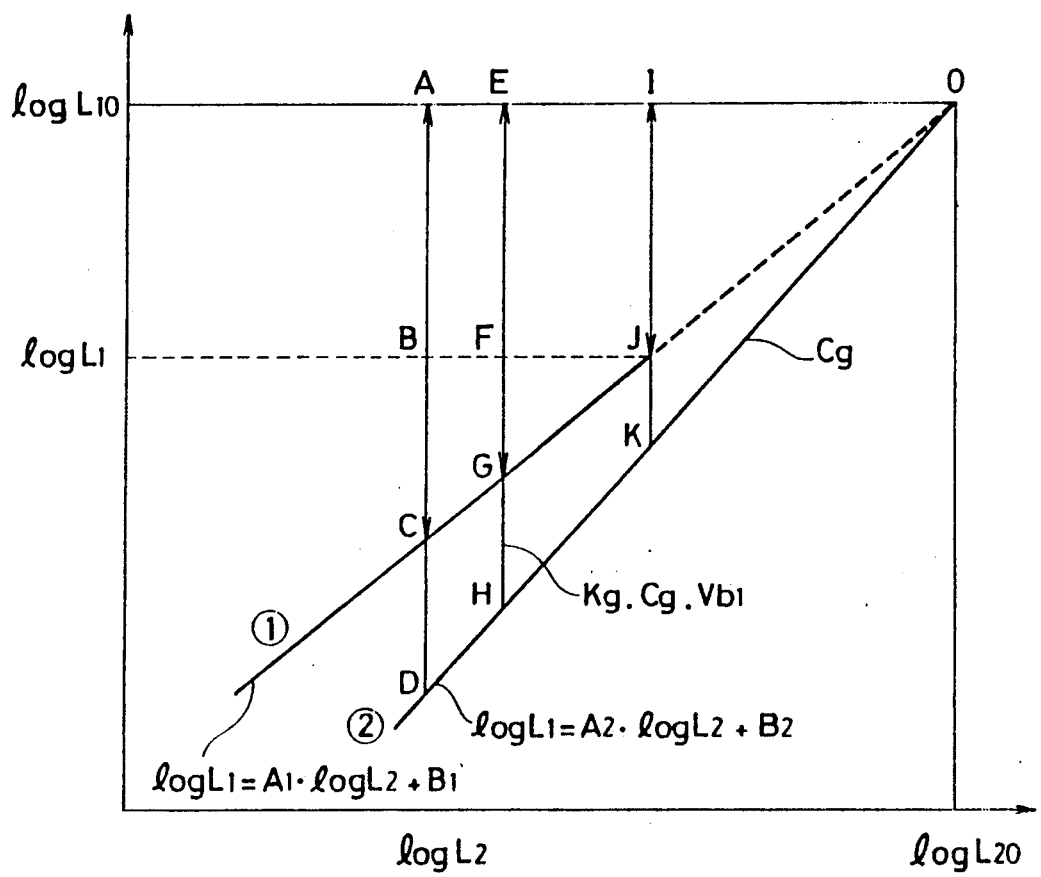

Referring to FIG. 4, a straight line ① represents a calibration curve before an injection of the specific dye, while another straight line ② represents a calibration curve taken at an arbitrary short time period after an injection of the specific dye. The straight line ② provides calibration for a short time period, and hence the specific dye is taken to be constant. The straight line ②, considered similarly to the expression (5), is expressed as follows:

$$\log L_1 = A_2 \cdot \log L_2 + B_2$$

The intersection 0 of the straight lines 1 and 2 is considered to be an ischemic point at which there is substantially no blood in the tissue. This bloodless point is expressed as follows:

$$\log L_{10} = (A_1 \cdot B_2 - A_2 \cdot B_1)/(A_1 - A_2)$$

From FIG. 4 it is seen that $$GH/CD = OG/OC = OE/OA = EG/AC,$$

and $$GH/EG = CD/AC.$$

Hence, $$kg \cdot Cg \cdot Vb_1/Vb_1 = kg \cdot Cg \cdot Vb_2/Vb_2$$

Thus, $$GH/EG = kg \cdot Cg = CD/AC$$

whereby the dye concentration in the blood can be measured.

Normalizing as Y-axis $\log L_{10}$ of the intersection 0 between the straight lines ① and ②, the blood volume Vb is expressed as follows:

$$Vb = 1 + \frac{\log L_{10} - (A_1 \cdot \log L_2 + B_1)}{\log L_{10}} \quad (10)$$

Hence, a signal Cg corresponding to a voltage representing the specific dye concentration, can be found by the expressions (7) and (10) as follows:

$$Cg = \frac{\log L_{10} \cdot [\log L_{10} - (A_1 \cdot \log L_2 + B_1)]}{2 \cdot \log L_{10} - (A_1 \cdot \log L_2 + B_1)} \quad (11)$$

Using the method of least squares, the above expression for Cg can be expressed as a simulation curve plotted over time. The simulation curve is expressed as follows:

$$Cg = Ae^{-Bt} \quad (12)$$

wherein t represents the elapsed time after injection of the specific dye and symbols A and B represent constants.

The constants A and B are found by the above expression (12). The blood plasma disappearance rate k and the retention rate R % are expressed as follows:

$$k = B \quad (13)$$

$$R \% = e^{-BT} \quad (14)$$

wherein T represents the elapsed time in minutes after injection of the dye. These two rates characteristically express the intake of the specific dye into the liver. Since the retention rate applies to an elapsed time of T minutes, this retention rate may be referred to as the "T-minute retention rate".

While the biocalibration employed in the present invention has been described above, an embodiment of the present invention employing the aforementioned biocalibration will now be described.

Figure 5:
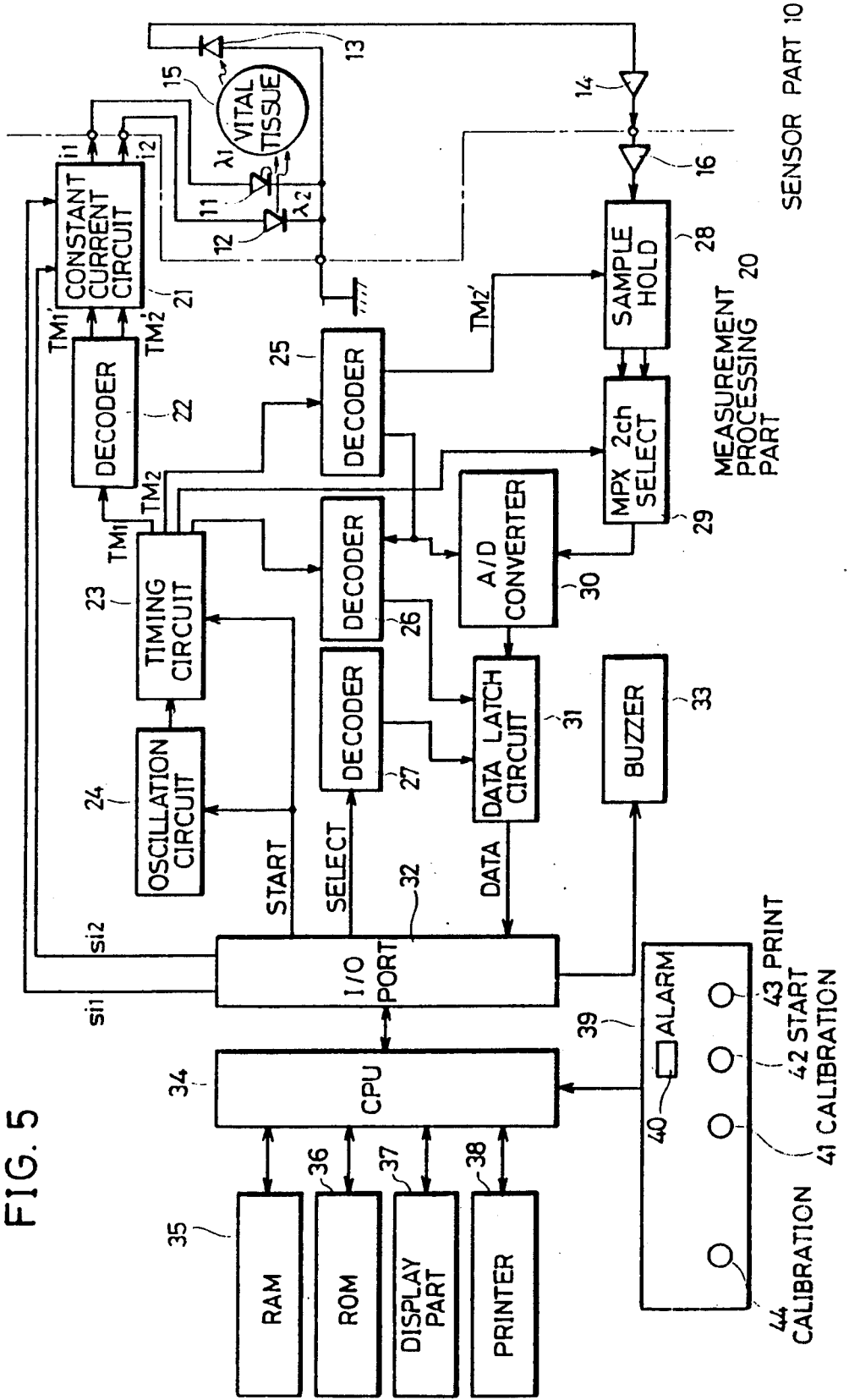
FIG. 5 is a schematic block diagram showing the entire structure of an embodiment of the present invention.
Figures 6, 7:
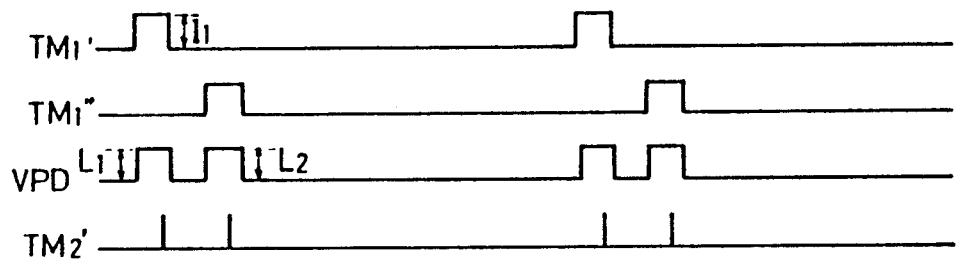
FIG. 6 is a timing chart for detecting quantities of light of wavelength $\lambda_1$ and $\lambda_2$ after passage through a prescribed optical path in a reference object.
FIG. 7 illustrates data stored in a RAM as shown in FIG. 5.

FIG. 5 is a schematic block diagram showing an embodiment of the present invention, FIG. 6 is a timing chart for detecting quantities of light of wavelengths $\lambda_1$ and $\lambda_2$ after passage through a prescribed optical path through a measured object, and FIG. 7 illustrates data stored in a RAM as shown in FIG. 5.

Referring to FIG. 5, the present liver function testing apparatus comprises a sensor section or part 10 and a measurement processing part or section 20. The sensor part 10 includes a first light source 11, a second light source 12, a light receiving element 13 and a preamplifier 14. The first light source 11 generates optical pulses $I_1$ having a wavelength $\lambda_1$ having a large absorbance to a specific dye. The second light source 12 generates optical pulses $I_2$ having a wavelength $\lambda_2$ having no absorbance to the specific dye. The light receiving element 13 receives light applied to vital tissue 15 from the light sources 11 and 12 to pass through a prescribed optical path through the tissue 15. The light sources 11 and 12 are driven by the measurement processing part 20 to alternately emit light by pulse operation, respectively.

The measurement processing part 20 includes a CPU 34 which serves as arithmetic means. The CPU 34 supplies a start signal to an oscillation circuit 24 and to a timing circuit 23 through an I/O port 32. The oscillation circuit 24 produces a prescribed clock signal. This clock signal and the aforementioned start signal are utilized to supply a constant current $i_1$ to the first light source 11 and a constant current $i_2$ to the second light source 12, from a constant current circuit 21 through the timing circuit 23 and a decoder 22 at timing $TM_{1'}$ and $TM_{1''}$ as shown in FIG. 6.

The light $I_1$ emitted form the first light source 11 and the light $I_2$ emitted from the second light source 12 pass through the prescribed optical path in the vital tissue 15, to be incident upon the light receiving element 13. A current generated from the light receiving element 13 is supplied to the preamplifier 14 performing a current-to-voltage conversion and amplifying the signal to be supplied to the measurement processing part 20. Output of the preamplifier 14 is amplified to a level within a prescribed range by an amplifier 16 provided in the measurement processing part 20, whereby an output such as $V_{PD}$ shown in FIG. 6 is obtained. A sample and hold circuit 28 samples and holds the output from the amplifier 16 on the basis of a timing signal $TM_{2'}$, shown in FIG. 6, generated by the timing circuit 23 and a decoder 25.

The signal thus sampled and held is selected by a multiplexer 29 and converted into a digital signal by an A-D converter 30, to be data-latched by a data latch 31. At this time, the multiplexer 29, the A-D converter 30 and the data latch 31 are controlled in timing by the timing circuit 23 and the decoder 26.

The latched data are timed by a decoder 27 through a select signal outputted from the CPU 34 through the I/O port 32, for storing in a RAM 35 as digital signals $L_1$ and $L_2$. The I/O port 32 is connected with a buzzer 33, which provides a reminder or timing signal for injecting the specific dye. Further, the CPU 34 is connected with the RAM 35, a ROM 36, a display part 37 and a sample and hold circuit 28. The RAM 35 is adapted to store data as shown in FIG. 7 as hereinafter described, and the ROM 36 stores programs based on flow charts shown in FIGS. 8A to 8D as hereinafter described. The display part 37 displays data as shown in FIGS. 9 to 12, as hereinafter described. A printer 38 is adapted to print the result of a liver function test.

A function section 39 includes an alarm LED 40, first and second calibration keys 41 and 44, a start key 42 and a print key 43. The alarm LED 40 is adapted to display an alarm when the reliability of the test result is small. The first calibration key 41 is adapted to set a first biocalibration mode before injection of a specific dye. The second calibration key 44 is adapted to set a second biocalibration mode after injection of the specific dye. The start key 42 provides a starting command signal to start a measurement mode. The print key 43 is adapted to provide a printout of the test result.

In the aforementioned exemplary structure shown in FIG. 5, the light emitted from the first and second light sources 11 and 12 to pass through the prescribed optical path in the vital tissue 15, is received by a single light receiving element 13. However, the invention is not restricted to this example. Rather, light receiving elements may be provided in correspondence to the first and second light sources 11 and 12 respectively, to sample outputs of the respective light receiving elements, thereby to read the respective sampling outputs by the CPU 34 in a time-sharing manner. Alternately, a single light source commonly emitting light having a wavelength $\lambda_1$ absorbed by specific dye and light having a wavelength $\lambda_2$ not absorbed by the same, may be provided as light source means, with provision of two filters for individually transmitting the light of the respective wave-lengths and light receiving elements corresponding to the respective ones of the filters.

Figure 12:
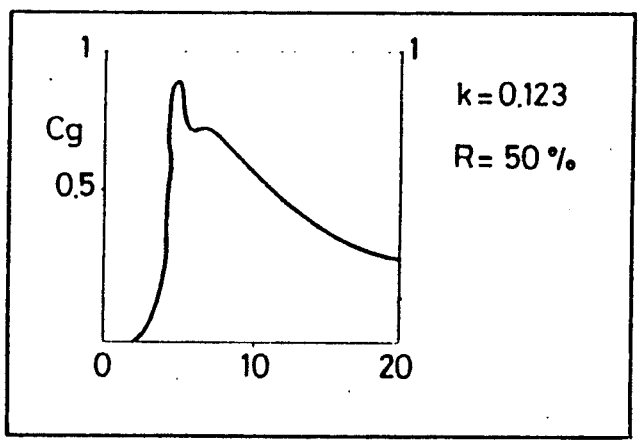
Figure 13:
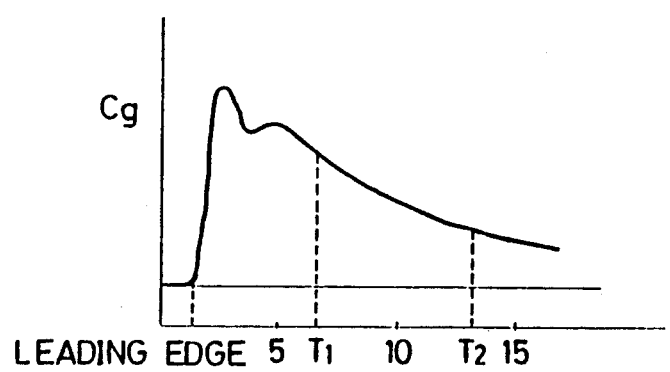
FIG. 13 shows an example of a disappearance curve of a specific dye measured according to the present invention.

FIG. 7 illustrates data stored in the RAM 35 as shown in FIG. 5, and FIGS. 8A to 8D are flow charts for illustrating a concrete operation of the embodiment of the present invention, while FIGS. 9 to 12 are illustrative of exemplary displays on the display part 37 shown in FIG. 5, FIG. 13 is illustrative of an exemplary disappearance curve of a specific dye, and the blood plasma disappearance rate k and the "T-minute retention rate" R % measured by the present apparatus.

With reference to FIGS. 5, 8A to 8D and 13, the operation of the embodiment of the present invention will now be described.

The operation of the present apparatus includes a data sampling mode, first and second biocalibration modes, an initiating mode and a measurement mode. FIGS. 8A, 8B, 8C and 8D show the operation flows of these modes respectively.

Figure 8A:
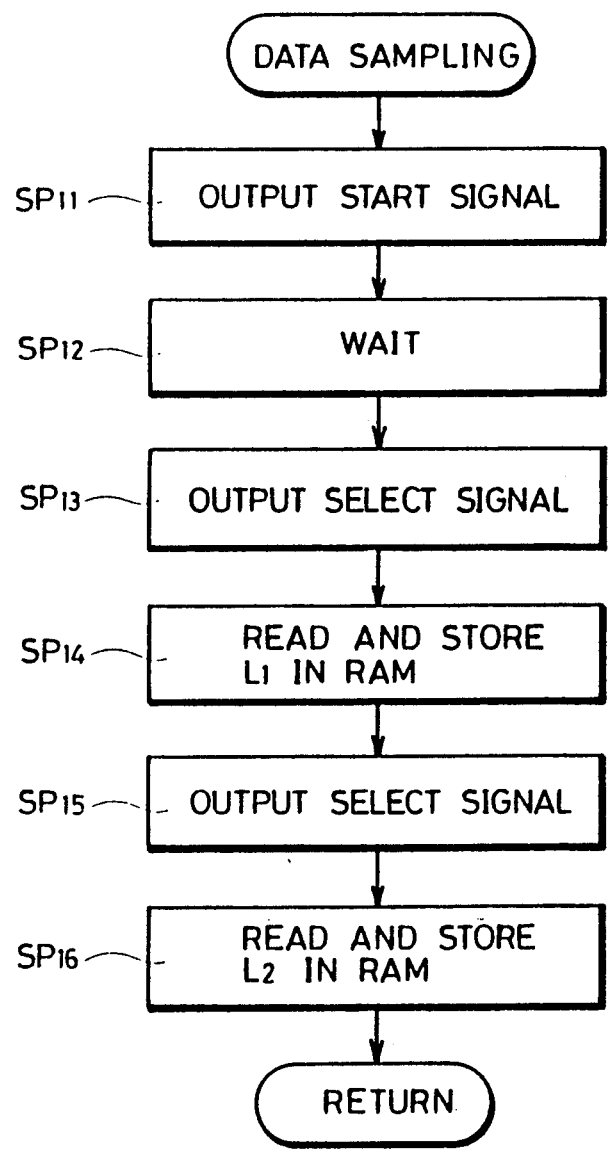

First, it is pointed out that the data sampling mode shown in FIG. 8A is executed as subroutines in the biocalibration modes and the measurement mode as hereinafter described. Steps, abbreviated as SP in the figures, SP11 to SP16 are adapted to quantities of light $I_1$, $I_2$ of a pair of wavelengths $\lambda_1$ and $\lambda_2$ after passage through a measured object and store the same in the RAM 35. Namely, the CPU 34 outputs the start signal from a line shown in FIG. 5 through the I/O port 32 at the step SP11. The values $L_1$ and $L_2$ are data-latched by the start signal, as hereinabove described. The CPU 34 waits until the data are latched at the step SP12.

Then, at the step SP13, the CPU 34 outputs the selected signal to a selected line shown in FIG. 5 through the I/O port 32, to read the data of $L_1$ through the I/O port 32 at the step SP14, thereby to store the same in a storage area $8a1$ of the RAM 35 as shown in FIG. 7.

Similarly, the CPU 34 stores the data of $L_2$ in a storage area $8a2$ of the RAM 35 at the steps SP15 and SP16.

Upon completion of the aforementioned operation at the step SP16, the CPU 34 returns to the original step. This will be described with reference to FIG. 8B showing the biocalibration mode and FIG. 8D showing the measurement mode.

Figure 8B:
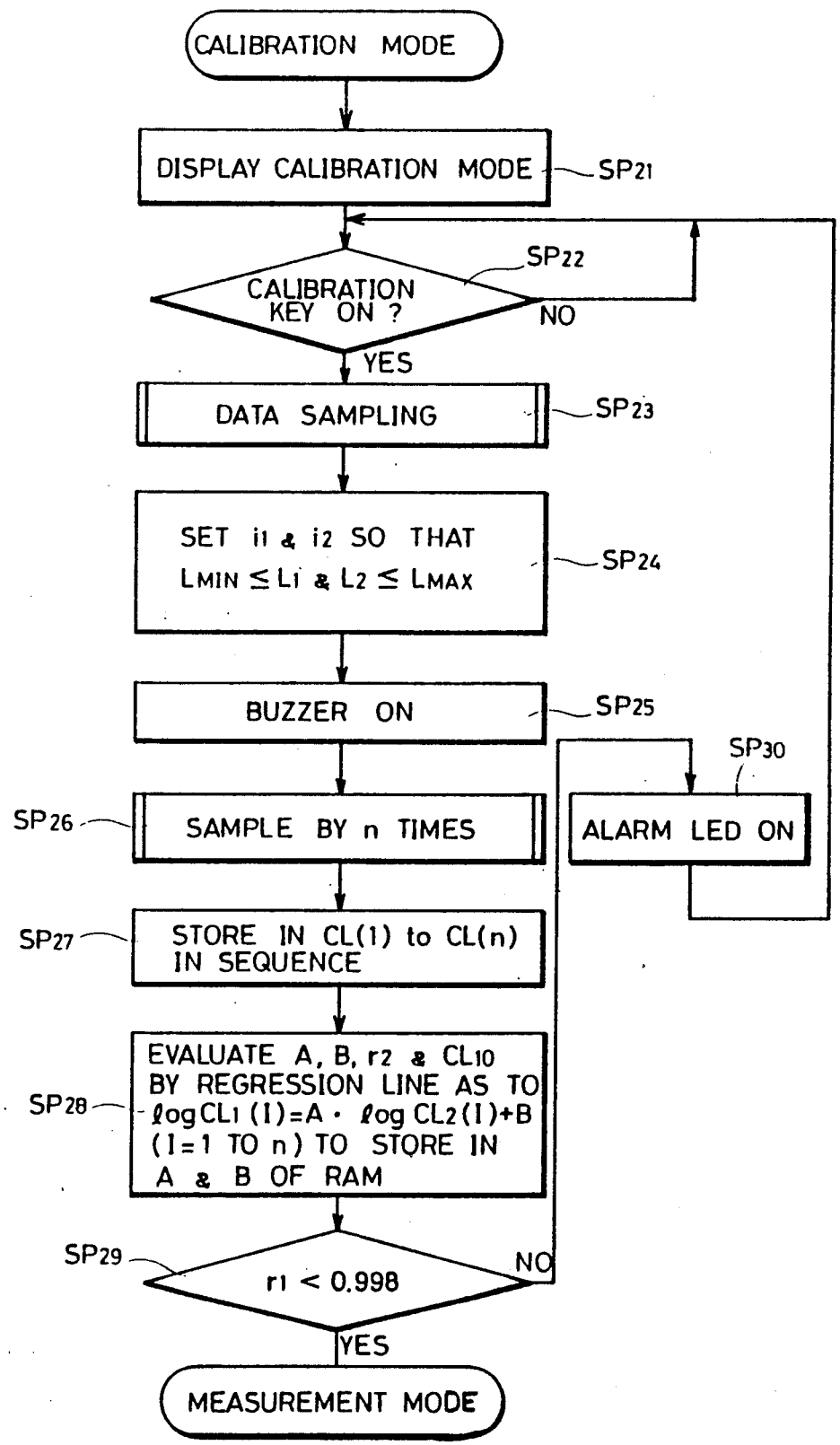

FIG. 8B shows the operation flow chart of the first biocalibration mode, which is started when power is supplied to the apparatus or upon completion of the operation of the measurement mode shown in FIG. 8D as hereinafter described. At a step SP21, the CPU 34 makes the biocalibration mode appear on the display part 37. This display shows that the apparatus enters the biocalibration mode and indicates that the sensor part 10 should now be attached to a tissue 15, as shown in FIG. 9, for example. In accordance with this indication, an operator attaches the sensor part 10 to the vital tissue 15.

Thereafter the CPU 34 waits until the calibration key 41 is operated at a step SP22. When the calibration key 41 is operated, the CPU 34 advances to a step SP23, to execute the data sampling subroutine shown in FIG. 8A, as hereinabove described.

Then, the CPU 34 controls the constant current circuit 21 as shown in FIG. 5 so that the data $L_1$ and $L_2$ read at the step SP23, are within ranges of light quantity data $L_{MAX}$ and $L_{MIN}$ stored in storage areas $8b1$ and $8b2$ of the RAM 35. The CPU 34 then stores current set values $i_1$ and $i_2$ in storage areas $8c1$ and $8c2$ in the RAM 35. Thereafter the currents $i_1$ and $i_2$ regularly flow to the light sources 11 and 12. Initializing operation for the aforementioned currents will be described in further detail with reference to FIG. 8C.

Then, the CPU 34 sounds the buzzer at a step SP25, to inform that initialization is completed. Subsequent steps SP26 to SP29 are shown in the flow chart for performing the aforementioned biocalibration. In more concrete terms, the CPU 34 samples the values of $L_1$ and $L_2$ n times respectively, at the steps SP26 and SP27, to cause $CL_1(l)$ to $CL_1(n)$ to be stored in storage areas $8dl$ to $8dn$ and $CL_2(l)$ to $CL_2(n)$ to be stored in storage areas $8el$ to $8en$. At the subsequent step SP28, the CPU 34 performs a regression line analysis with respect to $\log CL_1(I)$ and $\log CL_2(I)$ ($I=1$ to $n$), in accordance with the following operation expression:

$$\log CL_1(I) = A_1 \cdot \log CL_2(I) + B_1$$

The CPU 34 finds the values $A_1$ and $B_1$ in the above operation expression, a correlation coefficient $r_1$ and the maximum value of $CL_1(I)$ ($I=1$ to n) as $CL_{10}$, to store the same in storage areas 8f1, 8f2, 8f3 and 8f4 in the RAM 35 respectively.

Then, at the step SP29, the CPU 34 determines whether or not the correlation coefficient $r_1$ is at least 0.998 in order to verify the reliability of the biocalibration, advances to a step SP30 if the same is less than 0.998 to light the alarm LED 40, and returns to the step SP22 to again perform a biocalibration. On the other hand, if a determination is made that the correlation coefficient $r_1$ is at least 0.998, the CPU 34 advances to the measurement mode as shown in FIG. 8D. The reference value 0.998 of the correlation coefficient $r_1$ herein employed, is a mere example, which is determined by performance of the entire apparatus. During the data sampling that takes place n times at the step SP26, the testee raises and brings down his hand and presses the same by the sensor, in order to change the blood volume in the organism.

Figure 8C:
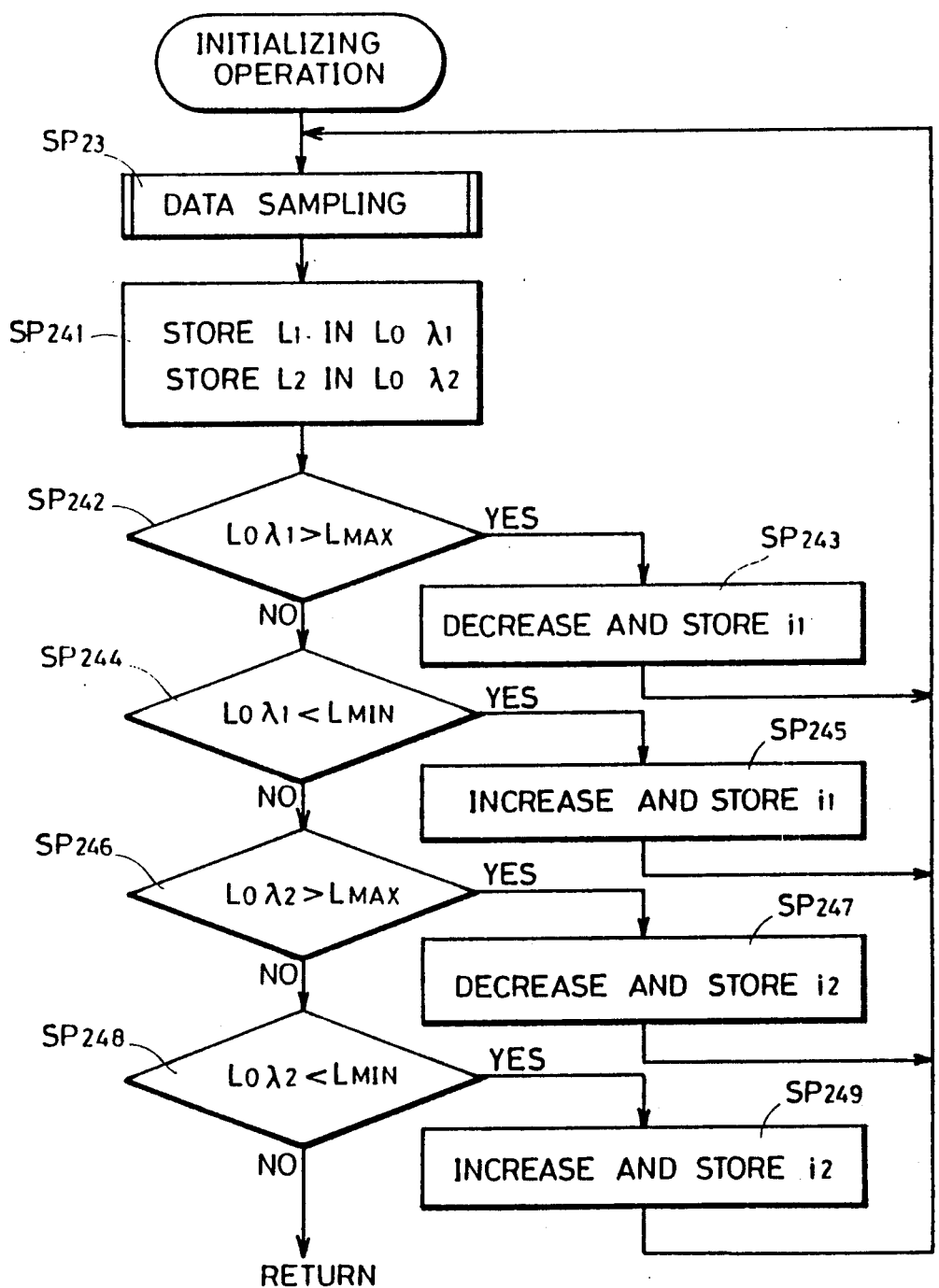
Figure 8D:
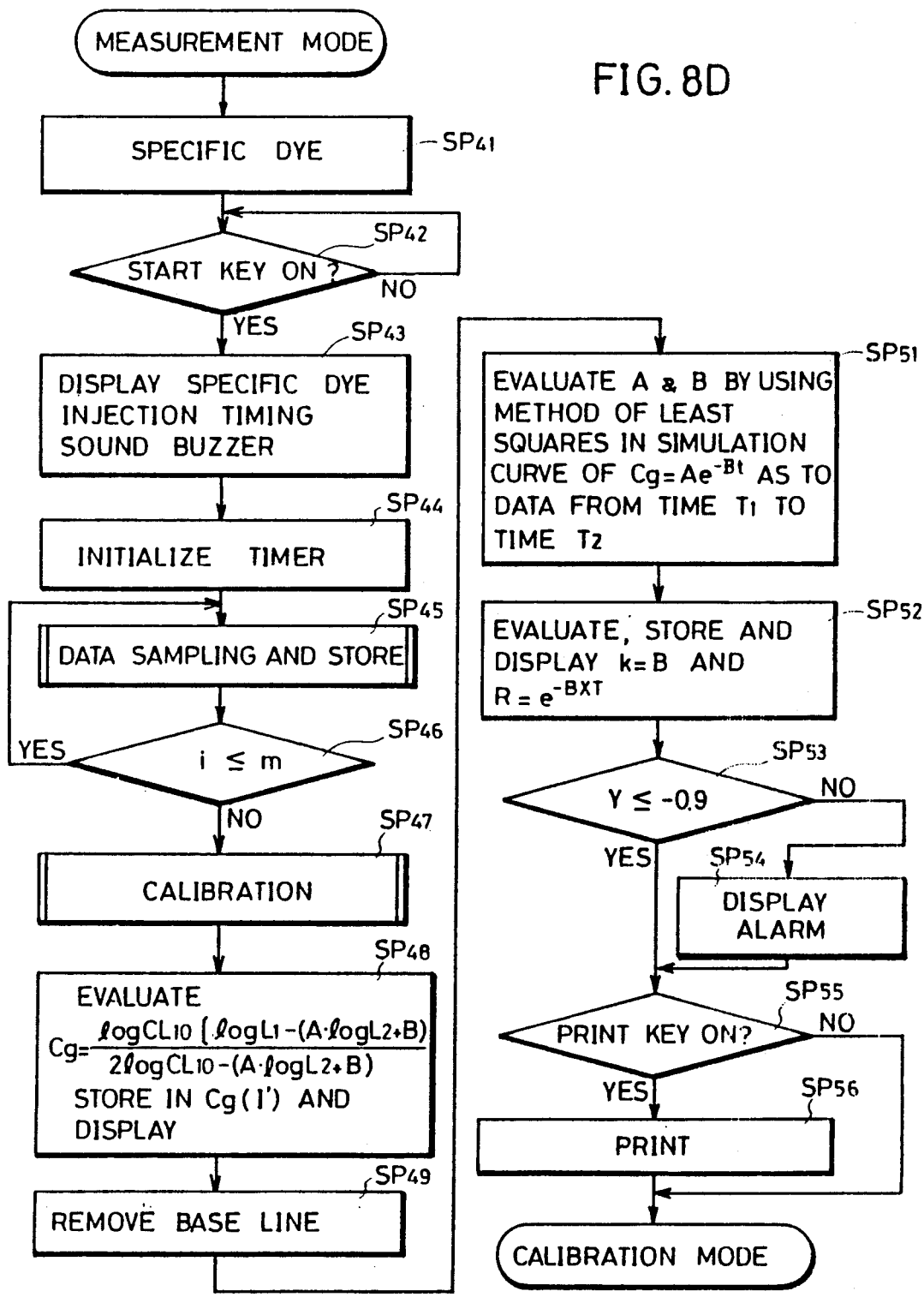

With reference to FIG. 8C, the aforementioned initializing operation at the step SP24 as shown in FIG. 8B will now be described in more detail.

The light quantity data $L_1$ and $L_2$ of the light of the wavelengths $\lambda_1$ and $\lambda_2$ are stored in the storage areas 8a1 and 8a2 of the RAM 35. At a step SP241, the CPU 34 stores the values of $L_1$ and $L_2$ in storage areas 8h1 and 8h2 in the RAM 35 as LO $\lambda_1$ and LO $\lambda_2$, respectively. Then the CPU 34 executes steps SP242 to SP249, to adjust the set values of the currents flowing from the constant current circuit 21, so that LO $\lambda_1$ and $\lambda_2$ are set between the light quantity data $L_{MAX}$ and $L_{MIN}$ ($L_{MAX} > L_{MIN}$) stored in the storage areas 8b1 and 8b2 of the RAM 35.

More specifically, if LO $\lambda_1$ is greater than $L_{MAX}$ at the step SP242, the CPU 34 advances to the step SP243 to set the current set value $i_1$ at a small value to again execute the steps SP23 and SP241, and a determination is again made as to whether or not $LO'_1$ is greater than $L_{MAX}$ at the step SP242. If LO $\lambda_1$ is less than $L_{MAX}$, the CPU 34 advances to the step SP244 to determine whether or not LO $\lambda_1$ is less than $L_{MIN}$. If LO $\lambda_1$ is less than $L_{MIN}$, the CPU 34 increases the value of the current set value $i_1$ at the step SP245, to return to the aforementioned step SP23. This operation is repeated to fix the current set value $i_1$ so that LO $\lambda_1$ is between $L_{MAX}$ and $L_{MIN}$.

Then, at the steps SP246 to SP249, the current set value $i_2$ is fixed so that LO $\lambda_2$ is between $L_{MAX}$ and $L_{MIN}$, similarly to the steps SP242 to SP245. Thus, the current set values $i_1$ and $i_2$ finally fixed din the steps SP23 to SP249 are stored in the storage areas 8c1 and 8c2 of the RAM 35.

The measurement mode will now be described with reference to FIG. 8D. At a step SP41, the CPU 34 displays on display 37 an instruction to prepare the injection of the specific dye, as shown in FIG. 10. In accordance with the display, the operator prepares for the injection of the specific dye into the testee. At a step SP42, the CPU 34 waits until the start key 42 is operated. Upon a determination that the start key 42 has been operated, the CPU 34 displays a timing signal for injecting the specific dye at a step SP43, while sounding the buzzer 33. This is displayed as 1→2→3→4→5 as shown in FIG. 11, for example, so that the measurer injects the specific dye upon display of "5". The CPU 34 generates a first sound by the buzzer 33 with the displays of "1", "2", "3" and "4", while generating a different sound by the buzzer 33 upon display of "5".

Upon generation of the sound and the display, the measurer injects the specific dye. The CPU 34 sets "0" as the initial value of a timer at a step SP44. Then, at a step SP45, the CPU 34 executes a data sampling program, which is the subroutine as hereinabove described with reference to FIG. 8A. Then, the sampling data are stored in the storage areas 8a1l to 8aln and 8a2l to 8a2n of the RAM 35 as $L_1(l)$ to $L_1(n)$ and $L_2(l)$ to $L_2(n)$, respectively. One sampling time ITM is expressed as: ITM=TS/(m-l), wherein m represents the sampling number of the disappearance curve of the specific dye, I represents an integer between 1 to m, and wherein TS represents a measuring time of the disappearance curve. This coincides with the injection time of the specific dye if I=1, as a matter of course. The CPU 34 determines whether or not i is greater than m at a step SP46 and returns to the step SP45 if i is less than m, to repeat the sampling and storing. Upon a determination that i is greater than m, the CPU 34 advances to a step SP47 and performs a second biocalibration similarly to the above description with reference to FIG. 8B, to obtain constants $A_2$ and $B_2$ and a correlation function $r_2$ and store the same in the storage areas 8f5, 8f6 and 8f7 of the RAM 35 respectively. The second biocalibration is not restricted to the step SP47, but may be performed at the steps SP45 and SP46 in a uniformly distributed state of the ICG concentration in the blood after the injection of the ICG. This second calibration may be initiated through the calibration key 44 shown in FIG. 5.

At a step SP48, the CPU 34 performs an operation based on the following operation expression by using the constants $A_1$, $B_1$, $A_2$ and $B_2$ obtained in the first and second biocalibration modes as hereinabove described and stored in the storage areas 8f1, 8f2, 8f5 and 8f6 of the RAM 35 to store Cg(I) in a storage area 8gl to 8gm of the RAM 35:

$$Cg(I) = \frac{\log CL_{10} [\log L_{10}(I) - (A_1 \cdot \log L_2(I) + B_1)]}{2\log CL_{10} - (A_1 \cdot \log L_2(I) + B_1)};$$

$$\log L_{10} = (A_1 \cdot B_2 - A_2 \cdot B_1)/(A_1 - A_2)$$

The value of Cg(I) is displayed on the display part 37 at the step SP48 in a mode shown in FIG. 12, for example. Referring to FIG. 12, the abscissa indicates the elapsed time from the injection of the specific dye and the ordinate indicates the value of Cg(I). The data Cg(I) stored in the storage areas 8gl to 8gm of the RAM 35 draw a disappearance curve of the specific dye as shown in FIG. 13, for example, and the leading edge thereof is detected, so that data preceding the same are subtracted as baselines from the respective values of Cg(I) at a step SP49, to be again stored in the storage areas 8gl to 8gm. The data sampling times $T_1$ to $T_2$ at the step SP45 may be average values of k times, in order to improve the accuracy of the measurement.

Then, at a step SP51, the CPU 34 finds the constants A and B by using the method of least squares in a simulation curve of:

$$Cg(I) = Ae^{-Bt}$$

$$I = Ts/(m-l)(\min.)$$

with respect to data between times $T_1$ to $T_2$ ($0 < T_1 < T_2 < Ts$) within the data Cg(I) stored in the storage areas 8gl to 8gm.

Then, the CPU 34 performs an operation of the blood plasma disapperance rate k=B and the "T-minute retention rate" R %=$e^{-BT}$ at a step SP52, to evaluate k and R %. The values k and R % thus evaluated are stored in storage areas 8j1 and 8j2 of the RAM 35, respectively. At this time, the CPU 34 processes a correlation coefficient $r_2$ by the method of least squares and stores the resulting correlation coefficient $r_2$ in a storage area 8j3 of the RAM 35. The CPU 34 further generates an end sound through the buzzer 33.

Further, the CPU 34 displays the values k and R % on the display part 37 in a mode shown in FIG. 12, for example. Then, at a step SP53, the CPU 34 determines whether or not the correlation coefficient $r_2$ is less than 0.95, for example. This determination is made to check the degree of correlation, since the correlation is improved as the correlation coefficient $r_2$ approaches −1. The value −0.95 is provisionally between zero and −1, and reliability of the apparatus is improved as the value comes closer to −1.

If the correlation coefficient $r_2$ is greater than 0.9, for example, the CPU 34 determines that reliability is insufficient and lights up the alarm LED 40 at the step SP54. On the other hand, if the correlation coefficient $r_2$ is less than −0.95, for example, at the step SP53, the CPU 34 advances to a step SP55 without flashing the alarm LED 44, since the measurement is reliable. At the step SP55, the CPU 34 determines whether or not the print key 43 is operated, to cause the printer 38 to print the values k and R % if the determination is: YES.

If necessary, the CPU 34 causes the printing of the characteristic dye disappearance curves of Cg(I) stored in the storage areas 8gl to 8gn of the RAM 35 and advances to the first biocalibration mode shown in FIG. 8B. Also when a determination is made that the print key 43 is not operated at the step SP55, the CPU 34 advances to the first biocalibration mode.

Figure 14A:
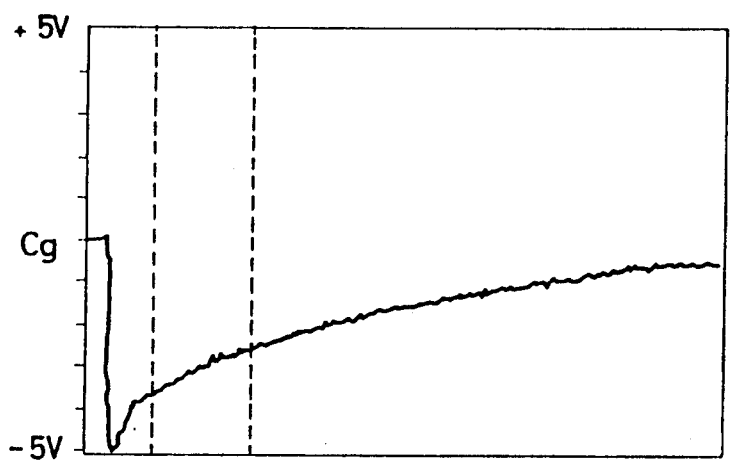
FIG. 14A illustrates a relationship between a disappearance curve, a blood plasma disappearance rate and a 15-minute retention rate measured according to the present invention.
Figure 14B:
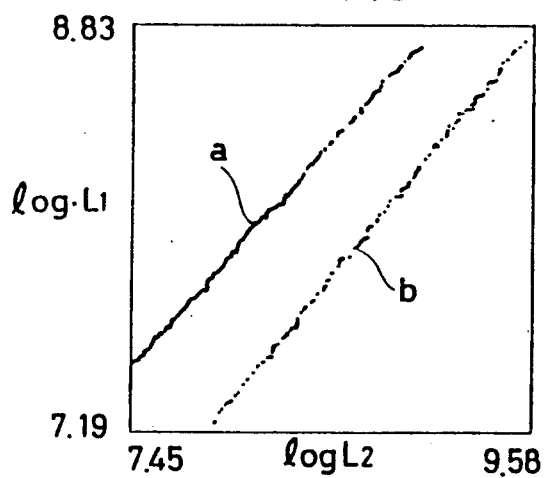
FIG. 14B illustrates light values $L_1$ and $L_2$ measured according to the present invention and two calibration curves.

FIG. 14B illustrates two experimental calibration curves of two whereby curve a represents the experiment before the dye injection and curve b is a calibration curve representing the experiment after a prescribed period of time has passed following the injection.

Figure 15:
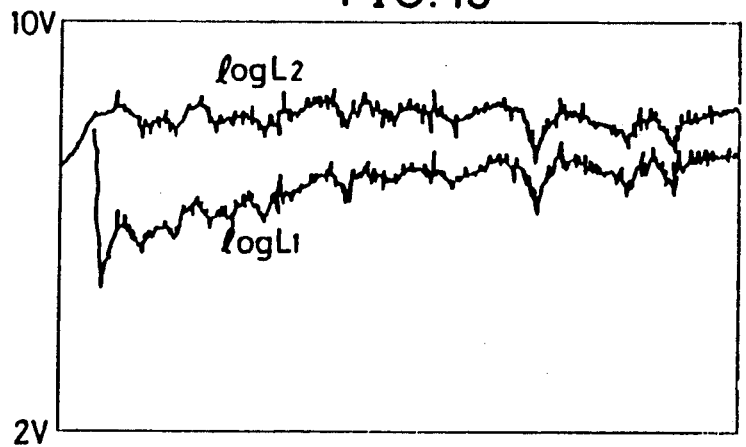
FIG. 15 illustrates light values $L_1$ and $L_2$ measured according to the present invention.

In the experiment shown in FIG. 14A, the sensor part 10 was attached to a left fingertip of a male patient age: 66, weight: 48 Kg, having a hepatic disease. An aqueous solution containing 24 mg of ICG (0.5 mg per Kg) was intravenously injected into the vein of his right lower arm. FIG. 15 shows the time change of $L_1$ and $L_2$ while employing a diode emitting light having a wavelength $\lambda_1 = 810$ nm as the first light source 11, and a diode emitting light at a wavelength $\lambda_2 = 940$ nm as the second light source 12.

The value k calculated by the ICG disappearance curve was 0.09 as shown in FIG. 14A and the value R % was 24.1%, while the value k measured by the conventional blood collection method was 0.099 and the value R % was 22.6%, which is a substantial coincidence. FIG. 15 also shows raw data of $L_1$ and $L_2$. It is clearly understood from FIG. 14B that the blood volume in the organism fluctuated.

The value k obtained through the present invention can be extended to an apparatus for obtaining and calculating values k for various ICG doses.

According to the invention the above described biocalibrations are perfomed for obtaining the blood plasma disappearance rate of the specific dye and the retention rate on the basis of a plurality of sampling outputs during a prescribed period after injection of the specific dye and for obtaining the required coefficients of the regression line expressions and prescribed operation expressions. Thus, a correct time management of the disappearance curve of the specific dye is made possible to obtain correct data. Further, the blood plasma disappearance rate and the retention rate can be obtained not merely from several samples as is the case in the conventional blood sample taking method, but from a large number of disappearance curve data whereby the reliability of the data is improved.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A liver function testing apparatus for testing a liver function, comprising: light source means (11, 12) for exposing vital tissue to a first light signal capable of being absorbed by a specific dye injected into blood of said vital tissue, said dye to be taken in and removed by the liver, and to a second light signal capable of not being absorbed by said specific dye; photoelectric conversion means (13) for outputting first and second photoelectric conversion signals obtained from said vital tissue and corresponding to said first light signal and to said second light signal applied to said vital tissue by said light source means; sampling means (28) for sampling said first and second photoelectric conversion signals a plurality of times; first decision means (34, SP28) for determining a first coefficient of a first regression line expression between said first and second photoelectric conversion signals on the basis of variable components in said blood included in said first and second photoelectric conversion signals sampled by said sampling means a plurality of times before injection of said specific dye; second decision means (34, SP28) for determining a second coefficient of a second regression line expression between said first and second photoelectric conversion signals on the basis of variable components in said blood included in said first and second photoelectric conversion signals sampled by said sampling means a plurality of times after a lapse of a prescribed period; and arithmetic means (34) for storing a plurality of sampling signal outputs of said sampling means during a prescribed period of time following said injection of said specific dye for processing a value correlated with a specific dye concentration in said blood on the basis of said first and second coefficients of said first and second regression line expressions determined by first and second decision means for obtaining a coefficient of a simulation function as a function of time by using the method of least squares on the basis of said processed value correlated with said specific dye concentration, for obtaining a blood plasma disappearance rate of said specific dye and a retention rate of said specific dye in said prescribed period of time on the basis of said simulation function coefficient.

2. The liver function testing apparatus in accordance with claim 1, wherein
said second decision means determines (SP28) said second coefficient within a prescribed period following an injection of said specific dye in an arbitrary short period after a time when said specific dye is uniformly distributed in said blood.

3. The liver function testing apparatus in accordance with claim 1, wherein said arithmetic means includes means (SP48) for obtaining first dimensionless constants $A_1$ and $B_1$ by performing a regression line analysis in accordance with the following operation expression:

$$\log CL_1 = A_1 \cdot \log CL_2 + B_1,$$

wherein $CL_1$ and $CL_2$ represent average voltage values of said first and second photoelectric conversion signals sampled by said sampling means a plurality of times before injection of said specific dye, and obtaining second dimensionless constants $A_2$ and $B_2$ by performing a regression line analysis in accordance with the following operation expression:

$$\log CL_1' = A_2 \cdot \log CL_2' + B_2,$$

wherein $CL_1'$ and $CL_2'$ represent average values of said first and second photoelectric conversion signals sampled by said sampling means a plurality of times after a lapse of a prescribed period following an injection of said specific dye, for obtaining:

$$\log L_{10} = (A_1 \cdot B_2 - A_2 \cdot B_1)/(A_1 - A_2)$$

as a blood-free point signifying that said tissue is substantially free of blood.

4. The liver function testing apparatus in accordance with claim 3, wherein said arithmetic means includes means (SP48) for processing a value $Cg$ correlated with said specific dye concentration on the basis of said constants $A_1$ and $B_1$ and said blood-free point $L_{10}$ in accordance with the following operation expression:

$$Cg = \frac{\log L_{10} [\log L_{10} - (A_1 \cdot \log L_2 + B_1)]}{2 \log L_{10} - (A_1 \cdot \log L_2 + B_1)}.$$

5. The liver function testing apparatus in accordance with claim 4, wherein said arithmetic means includes means (SP48) for processing first constants $A_1$ and $B_1$ by performing a regression line analysis in accordance with the following operation expression:

$$\log CL_1 = A_1 \cdot \log CL_2 + B_1,$$

wherein $CL_1$ and $CL_2$ represent average voltage values of said first and second photoelectric conversion signals sampled by said sampling means a plurality of times before injection of said specific dye, for obtaining second constants $A_2$ and $B_2$ by performing a regression line analysis in accordance with the following operation expression:

$$\log CL_1' = A_2 \cdot \log CL_2' + B_2,$$

wherein $CL_1'$ and $CL_2'$ represent average voltage values of said first and second photoelectric conversion signals sampled by said sampling means a plurality of times within a prescribed period of time after injection of said specific dye in an arbitrary period after a time when said specific dye is uniformly distributed in said blood, for obtaining:

$$\log L_{10} = (A_1 \cdot B_2 - A_2 \cdot B_1)/(A_1 - A_2)$$

as a blood-free point signifying that said tissue is substantially free of blood.

6. The liver function testing apparatus in accordance with claim 4, wherein said arithmetic means includes means (SP51) for processing constants A and B on the basis of the following operation expression:

$$Cg = Ae^{-Bt},$$

wherein t represents said prescribed period of time after injection of said specific dye.

7. The liver function testing apparatus in accordance with claim 1, wherein said arithmetic means includes means (SP52) for solving the following operation expression:

$$K = B,$$

said solving operation being based on the fact that k represents said blood plasma disappearance rate.

8. The liver function testing apparatus in accordance with claim 1, wherein said arithmetic means includes means (SP52) for solving the following operation expression:

$$R\% = e^{-BT},$$

wherein R % represents said retention rate.

9. The liver function testing apparatus in accordance with claim 1, wherein
said decision means includes means for processing a correlation coefficient of said regression line expression,
said liver function testing apparatus further including informing means (33) for giving an alarm when said correlation coefficient processed by said means for operating said correlation coefficient is greater than a predetermined value.

10. The liver function testing apparatus in accordance with claim 1, wherein
said arithmetic means includes means for processing correlation coefficient of said simulation function,
said liver function testing apparatus further including informing means (33) for giving an alarm when said correlation coefficient of said simulation function is greater than a predetermined value.

11. The liver function testing apparatus in accordance with claim 1, further including mode selection means (41, 42) for selecting a biocalibration mode for performing an operation for determining said coefficient of said regression line expression by said decision means, and a measurement mode for performing an operation for processing said value correlated with said specific dye concentration by said arithmetic means.

12. The liver function testing apparatus in accordance with claim 11, further including arithmetic means for activating said decision means in response to a selection of said biocalibration mode by said mode selection means.

13. The liver function testing apparatus in accordance with claim 12, wherein said arithmetic means (34) include means for activating said arithmetic means in response to a selection of a measurement mode by said mode selection means.

14. The liver function testing apparatus in accordance with claim 1, further including set means (SP241-SP249) for setting intensity levels of said first light signal and said second light signal emitted from said light source means so that levels of said first and second photoelectric conversion signals are within a predetermined range.

* * * * *